(12) United States Patent
Miller

(10) Patent No.: US 11,484,433 B1
(45) Date of Patent: Nov. 1, 2022

(54) EXPANDABLE AND RETRACTABLE MENSTRUAL CUP

(71) Applicant: TULIA FEMININE CARE CO., St. Louis, MO (US)

(72) Inventor: Ariana D. Miller, St. Louis, MO (US)

(73) Assignee: Tulia Feminine Care Co., St. Louis, MO (US)

( * ) Notice: Subject to any disclaimer, the term of this patent is extended or adjusted under 35 U.S.C. 154(b) by 0 days.

(21) Appl. No.: 17/721,493

(22) Filed: Apr. 15, 2022

Related U.S. Application Data

(60) Provisional application No. 63/176,412, filed on Apr. 19, 2021.

(51) Int. Cl.
*A61F 5/455* (2006.01)
*A61F 5/44* (2006.01)

(52) U.S. Cl.
CPC .......... *A61F 5/4553* (2013.01); *A61F 5/4404* (2013.01)

(58) Field of Classification Search
CPC ........ A61F 5/4553; A61F 5/4404; A61F 6/08; A61F 5/455; A61F 5/4405
See application file for complete search history.

(56) References Cited

U.S. PATENT DOCUMENTS

| | | | |
|---|---|---|---|
| 6,168,609 B1 * | 1/2001 | Kamen | .................. A61F 5/4553 600/573 |
| 10,188,543 B2 | 1/2019 | Lin | |
| 2018/0028350 A1 | 2/2018 | Wilson et al. | |
| 2019/0125571 A1 * | 5/2019 | Hu | .......................... A61F 5/4553 |
| 2021/0069009 A1 * | 3/2021 | Im | .......................... A61F 5/4553 |

FOREIGN PATENT DOCUMENTS

WO   2019211802 A1   7/2019

OTHER PUBLICATIONS

"Peachlife Ring Pull Menstrual Cup—Reusable 12 Hour Tampon Alternative PEACHCUP," Amazon.com. https://www.amazon.com/Menstrual-Cup-Ring-Easy-Removal/dp/B0789DSWGH/ref=sr_1_38?dchild=1&keywords=menstrual+cup&qid=1612039725&sr=8-38 [Date accessed: Jan. 28, 2021].

(Continued)

*Primary Examiner* — Philip R Wiest
*Assistant Examiner* — Alessandro R Del Priore
(74) *Attorney, Agent, or Firm* — Honda El-Jarrah; Bold IP, PLLC

(57) ABSTRACT

A menstrual cup is provided whose body can expand to reveal an interior cavity in an open position configured to receive menstrual fluids and that can retract to a closed position such that the interior cavity of the menstrual cup is contained by the sides and body of the menstrual cup and any contained fluids are prevented from leaking out. A hook is coupled to a bottom surface of the body of the menstrual cup and can be pulled upon to close the menstrual cup and pushed upwards to open the menstrual cup. The retractability of the menstrual cup facilitates insertion into the vaginal cavity and removal without spillage of menstrual fluids. The menstrual cup includes a body with retractable sides that can close inwardly. A user can grasp the hook to manipulate the body of the menstrual cup from either a closed position or an open position.

6 Claims, 8 Drawing Sheets

(56) References Cited

OTHER PUBLICATIONS

"Flex Cup," flexfits.com. https://flexfits.com/products/flex-cup?utm_source=google&gclid=Cj0KCQjwjN-SBhCkARIsACsrBz6vV0p7l2JmSn8WpbbHaiz8kFHDm2fObGsmm9EPCpVLw1u0q0mNBT0aAtC9EALw_wcB&utm_medium=cpc&utm_campaign=Search%20%7C%20US%20%7C%20Brand%20(Flexcup) [Date accessed: Dec. 22, 2020].

"Formoonsacup 2 cups + 1 cloth pad," menstrualcup.co. https://menstrualcup.co/shop/menstrual-cups/formoonsacup-pack/ [Date accessed: Dec. 22, 2020].

"Diva Cup," divacup.com. https://shopdiva.com/products/model-0 [Date accessed: Dec. 22, 2020].

"Say hello to the new Saalt Wear Go Bag." https://saalt.com/?gclid=Cj0KCQjwjN-SBhCkARIsACsrBz6S7LHNZqk8L6tA_tcl6DSgWWpD23fn4YSbCIZp7q0Gcjerzbc5vLoaAhBIEALw_wCB [Date accessed: Dec. 22, 2020].

"Lily Cup: The one that rolls as thin as a tampon," www.intimina.com. https://www.intimina.com/lily-cup?gclid=Cj0KCQjwjN-SBhCkARIsACsrBz4-bso4oOP2NdGqMQ5YXfbcqEsSygmEuBxAQzikxaX3OJStF5DhRTAaAjuPEALw_wCB [Date accessed: Dec. 22, 2020].

\* cited by examiner

EXPANDABLE AND RETRACTABLE MENSTRUAL CUP

CROSS-REFERENCE TO RELATED APPLICATIONS

This application is a non-provisional application which claims priority to U.S. Provisional Patent Application No. 63/176,412 filed on Apr. 19, 2021, which is incorporated by reference in its entirety.

FIELD OF THE DISCLOSURE

The present invention relates to a new method and system for a menstrual cup having a contracting and expandable body that is configured to contain menstrual fluid within the menstrual cup in an improved manner to avoid leakage or spilling upon removal and to facilitate insertion and removal of the menstrual cup through the inclusion of both a hook and the expandable/retractable body of the menstrual cup.

BACKGROUND

Menstrual cups currently available on the market rely upon the wearer manually folding the menstrual cup in order to insert into a vaginal cavity to properly position the menstrual cup within the vaginal cavity and when taking out the menstrual cup from the vaginal cavity after the menstrual cup is full. There are many challenges with such menstrual cups. One challenge is that it is very difficult to insert and remove the menstrual cup and users often experience great discomfort when the menstrual cup is located in place. Further, to remove the menstrual cup, there is often a great deal of leaking and spilling of any menstrual fluid contained within the menstrual cup when removing the cup, which can cause an undesirable and unhygienic mess on the user's hands and/or surrounding environment.

There are some menstrual cups that have made some attempts to improve upon traditionally available products. For example, the FLEX CUP enables the user to pull a cord at the bottom of the menstrual cup to pull the rim of the menstrual cup inwardly upon removal. The FLEX CUP is advertised as being similar to a tampon with its inclusion of the pull cord and is intended to facilitate easier grasping of the menstrual cup and removing the menstrual cup by grasping the pull cord. However, users still experience challenges in removing this menstrual cup and have noted that the insertion of the FLEX CUP remains as difficult, if not more challenging, due to the pull cord's connection to the rim of the menstrual cup. Also, pulling one side of the rim of the menstrual cup inward and downward during the removal process from the vaginal cavity increases the likelihood that the menstrual fluid will leak out of the menstrual cup if full.

The FORMOOSA CUP is another type of menstrual cup that has a rounder, ball-shaped cup body with a rim that extends downward into the menstrual cup, creating a double layer. This double layer is meant to prevent leaks of menstrual fluid by catching the fluid between the inner and outer layers of the menstrual cup. However, users have noted that the menstrual cup's less flexible and rounded shape still makes the menstrual cup exceedingly difficult to insert and remove, and still poses challenges and difficulties in use.

Accordingly, there is a need for an improved menstrual cup that may overcome some of the deficiencies described above and offer an improved solution for users who prefer to use menstrual cups to contain menstrual fluids during their periods.

SUMMARY

One or more non-limiting embodiments are provided for in the present description relating to a menstrual cup configured to collect menstrual fluid or other fluids from a vaginal cavity of a human body. In a non-limiting embodiment, the menstrual cup may comprise a flexible body having an interior cavity, whereby the flexible body is configured to open to an open position and to close and retract to a closed position. In a non-limiting embodiment, the menstrual cup may include a hook attached to a bottom surface located on an underside of the flexible body, whereby a downward force exerted by the hook on the flexible body causes the flexible body to contract and close inwardly such that a set of sides or a set of outer members of the flexible body are brought towards each other covering the interior cavity of the menstrual cup. In a non-limiting embodiment, an upward force exerted by the hook on the flexible body causes the flexible body to gradually expand outward such that the set of sides or the set of outer members of the flexible body expand outwards to a fully open position and exposing the interior cavity of the menstrual cup. In a non-limiting embodiment, the set of outer members are connected to each other by a set of connecting walls or pieces of the flexible body, whereby the set of outer members and the set of connecting walls or pieces define the interior cavity. In a non-limiting embodiment, each outer member of the set of outer members is connected to each connecting wall adjacent on each side of each outer member. In a non-limiting embodiment, the set of connecting walls are bendable and are configured to bend inwardly towards the interior cavity. Further, in a non-limiting embodiment, the set of sides or the set of outer members are visible from an exterior of the menstrual cup. Further, a bottom edge of each outer member of the set of outer members is connected to the bottom surface of the menstrual cup. In a non-limiting embodiment, when the flexible body of the menstrual cup is in the closed position, one or more sides of the set of outer members are in contact or touching each other. When the flexible body of the menstrual cup is in the closed position, one or more top surfaces of each outer member are contacting each other and the interior cavity of the flexible body of the menstrual cup is not accessible through the one or more top surfaces of each outer member. In a non-limiting embodiment, one or more interior pieces within the interior cavity are joined together and push upwards into the interior cavity of the flexible body of the menstrual cup when the flexible body of the menstrual cup is in the open position. Further, in a non-limiting embodiment, the hook includes a hook interior opening and a hook body encircling or surrounding the hook interior opening.

In a non-limiting embodiment, the present description further includes a method of using a menstrual cup. The method may further comprise providing the menstrual cup. The method may further comprise pulling or otherwise manipulating the hook of the menstrual cup to a close the set of sides or the set of outer members of the menstrual cup in order for the menstrual cup to be in the closed position and inserting the menstrual cup in the closed position into a vaginal cavity in a human body. Further, the method may include, upon positioning the menstrual cup at a desired spot within the vaginal cavity, pushing upwards on the hook in order for the set of sides or the set of outer members of the menstrual cup to fully expand while positioned inside of the vaginal cavity Further, the method may include, upon removal of the menstrual cup, grasping the hook to pull the menstrual cup out of the vaginal cavity causing the set of sides or the set of outer members to close or retract during removal of the menstrual cup, containing or enclosing by the set of sides or the set of outer members any collected menstrual fluids or other fluids within the menstrual cup, and disposing any of the collected menstrual fluids or other fluids collected in the internal cavity of the menstrual cup. Further, the method may include reusing the menstrual cup if needed or storing the menstrual cup for future use. The method may include upon insertion through the vaginal cavity, causing the set of sides or set of outer members to close inwardly prior to insertion of the menstrual cup in the vaginal cavity or opening. Upon removal of the menstrual cup from the vaginal cavity, the method may include causing the set of sides or set of outer members to close inwardly and then removing the menstrual cup from the vaginal cavity. The method may include washing or sanitizing the menstrual cup prior to reuse.

Other aspects and advantages of the invention will be apparent from the following description and the appended claims.

BRIEF DESCRIPTION OF THE DRAWINGS

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

DETAILED DESCRIPTION

The present description is drawn to an innovative menstrual cup that overcomes many deficiencies in the design and method of use of existing menstrual cups. The menstrual cup, as described in one or more non-limiting embodiments herein, may prevent leakage upon removal when the menstrual cup is full of menstrual fluid. In one or more non-limiting embodiments, the menstrual cup body is flexible and is designed to contract and be in a closed position where the sides are retracted and closed around an interior cavity of the menstrual cup for easier insertion within the body and for easier removal. In a closed position, the menstrual cup can also safely contain any menstrual fluids deposited in the interior cavity of the menstrual cup and helps to prevent spilling and leaking of the menstrual fluid during removal of the menstrual cup from a person's body and while trying to dispose of the menstrual fluid in a trash can, toilet, or other location for disposal of the menstrual fluid contained or captured in the menstrual cup.

In one or more non-limiting embodiments, the menstrual cup may be configured to expand and be in an open position when inserted into the vaginal cavity and in use. When the menstrual cup is removed, the menstrual cup may be configured to close and to contract upon removal and to close around any contained menstrual fluid as the menstrual cup is pulled down and out of the vaginal cavity, which prevents leakage and spillage of any contained menstrual fluid. Further, an advantage of the menstrual cup, as described herein in one or more non-limiting embodiments, is that the menstrual cup may further include a small hook on an underside of the menstrual cup which a user can grasp and take hold of when inserting the menstrual cup and positioning in place in a woman's vaginal cavity and grasp and take a hold of when removing from the vaginal cavity. The addition of this hook makes it much easier to manipulate and use the menstrual cup. Further details are provided with respect to the Figures.

Figure 1:
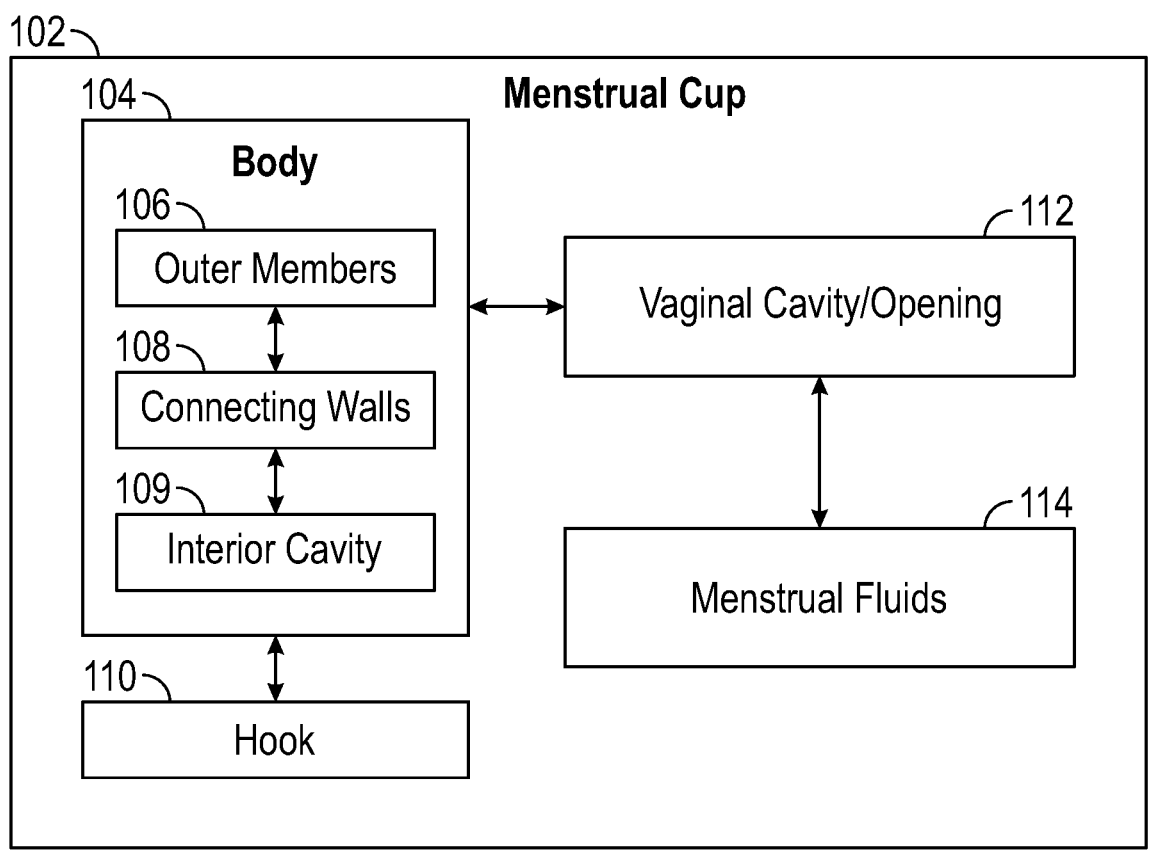
FIG. 1 depicts a block diagram of exemplary components of an exemplary menstrual cup.

FIG. 1 depicts a block diagram of one or more exemplary components of menstrual cup 102. In a non-limiting embodiment, menstrual cup 102 is a device that can be utilized to capture bodily fluids. In particular, the menstrual cup 102 is a device useful for capturing menstrual fluids 114 during a woman's period or menstrual cycle. The menstrual cup 102 is designed to be reusable. After each use, the menstrual cup 102 may be washed and sanitized for reuse and reinsertion in a woman's body to capture menstrual fluids 114 or if no further use is required, the menstrual cup 102 may be stored for later use.

Non-limiting examples of menstrual cup 102 are shown in FIGS. 2-7. In a non-limiting embodiment, any sides of the menstrual cup 102 may be configured to retract inwardly to close over and around an interior cavity 109 of the menstrual cup 102. Further, any sides of the menstrual cup 102 are configured to expand outwardly in particular after the menstrual cup 102 has been inserted within the vaginal cavity or opening 112 of a woman's body and positioned in place to capture any menstrual fluids 114. The same sides of the menstrual cup 102 may be configured to retract and contract and close around the interior cavity 109 of the menstrual cup 102 so that the interior cavity 109 is no longer accessible to receive any further menstrual fluids 114 in this closed position.

Figure 2:
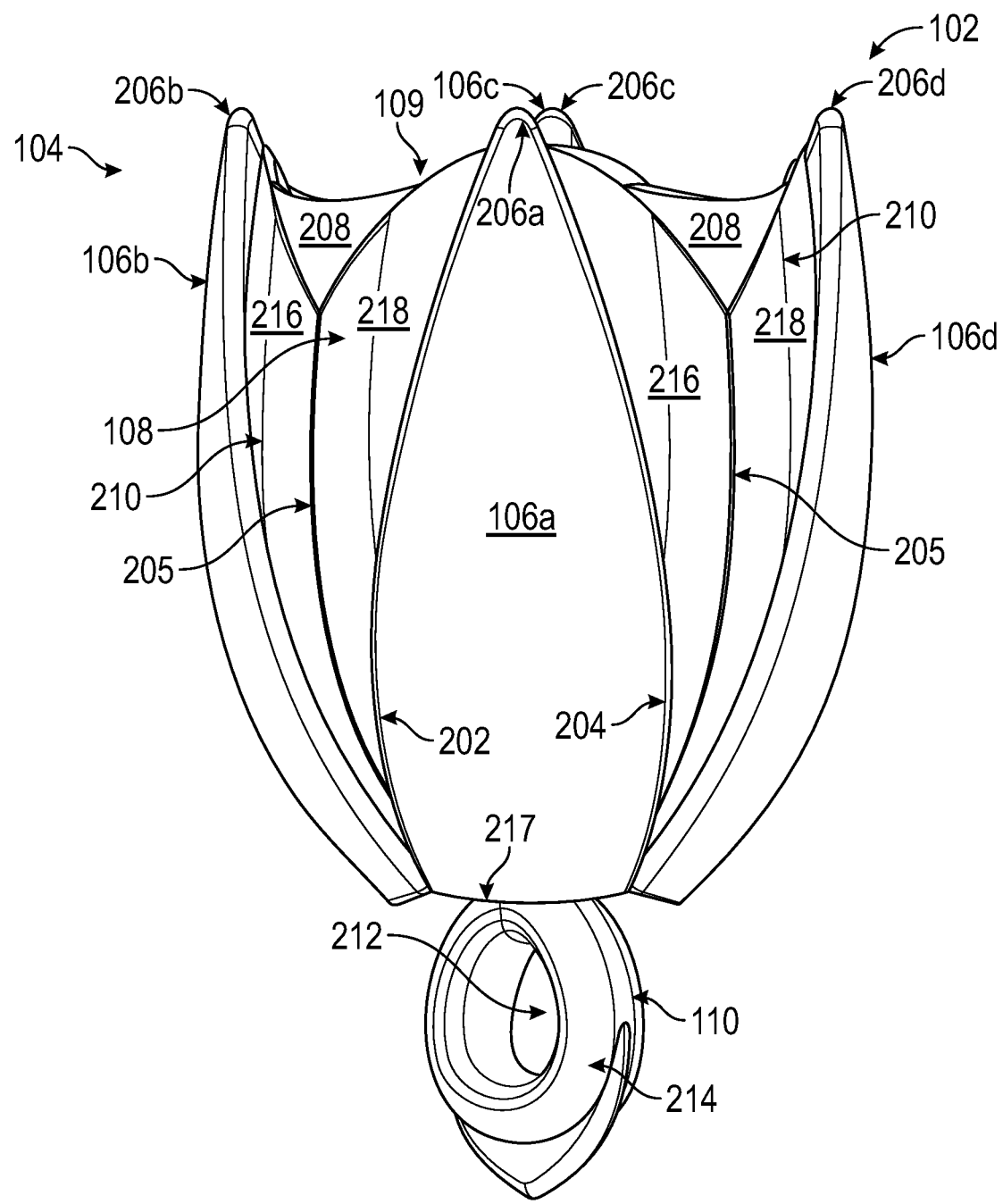
FIG. 2 depicts a pictorial illustration of a menstrual cup that includes a hook and a retractable body and is shown with the body of the menstrual cup in an open position.
Figure 3:
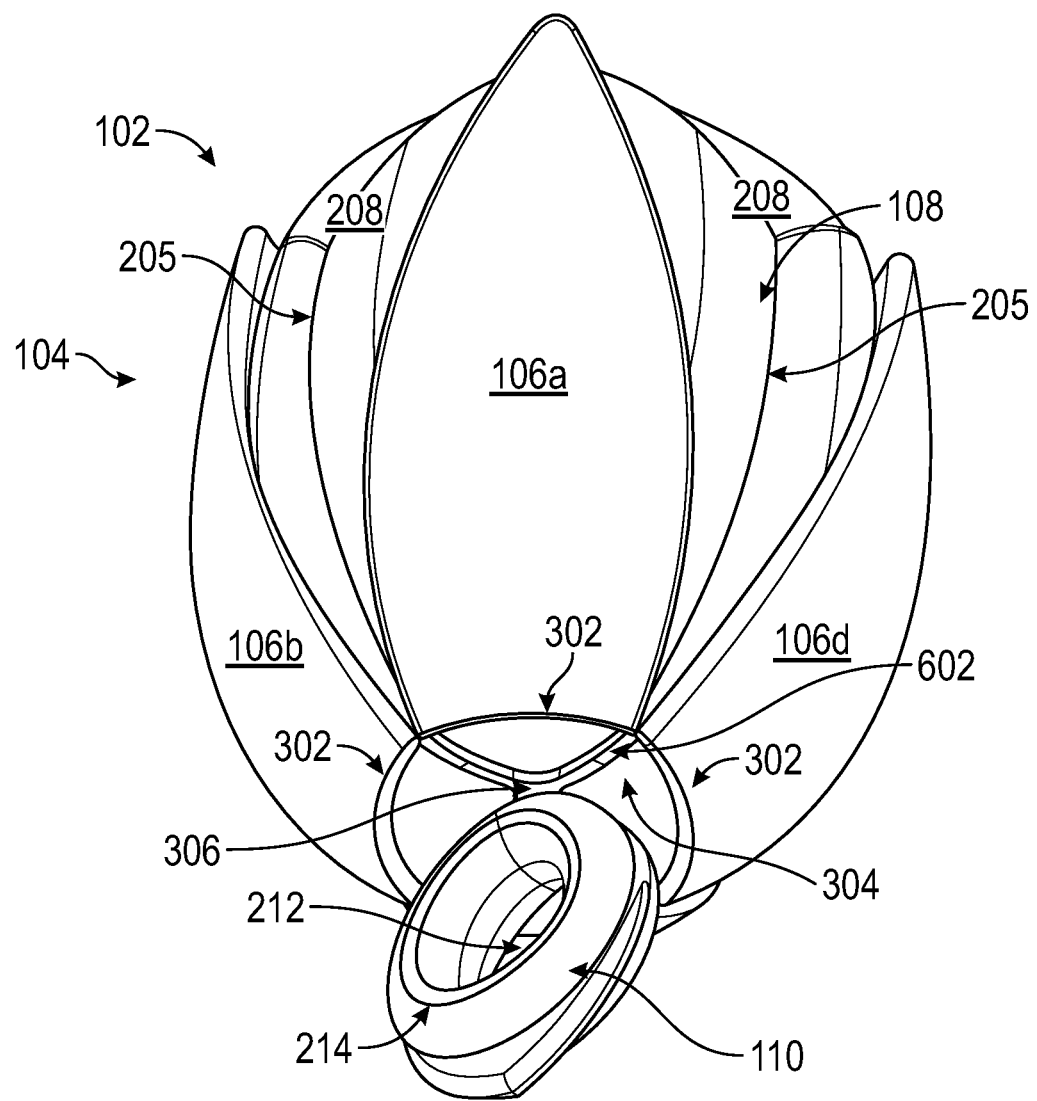
FIG. 3 depicts a pictorial illustration of the menstrual cup shown in FIG. 2 from a bottom perspective view and the body of the menstrual cup is shown in the open position.
Figure 4:
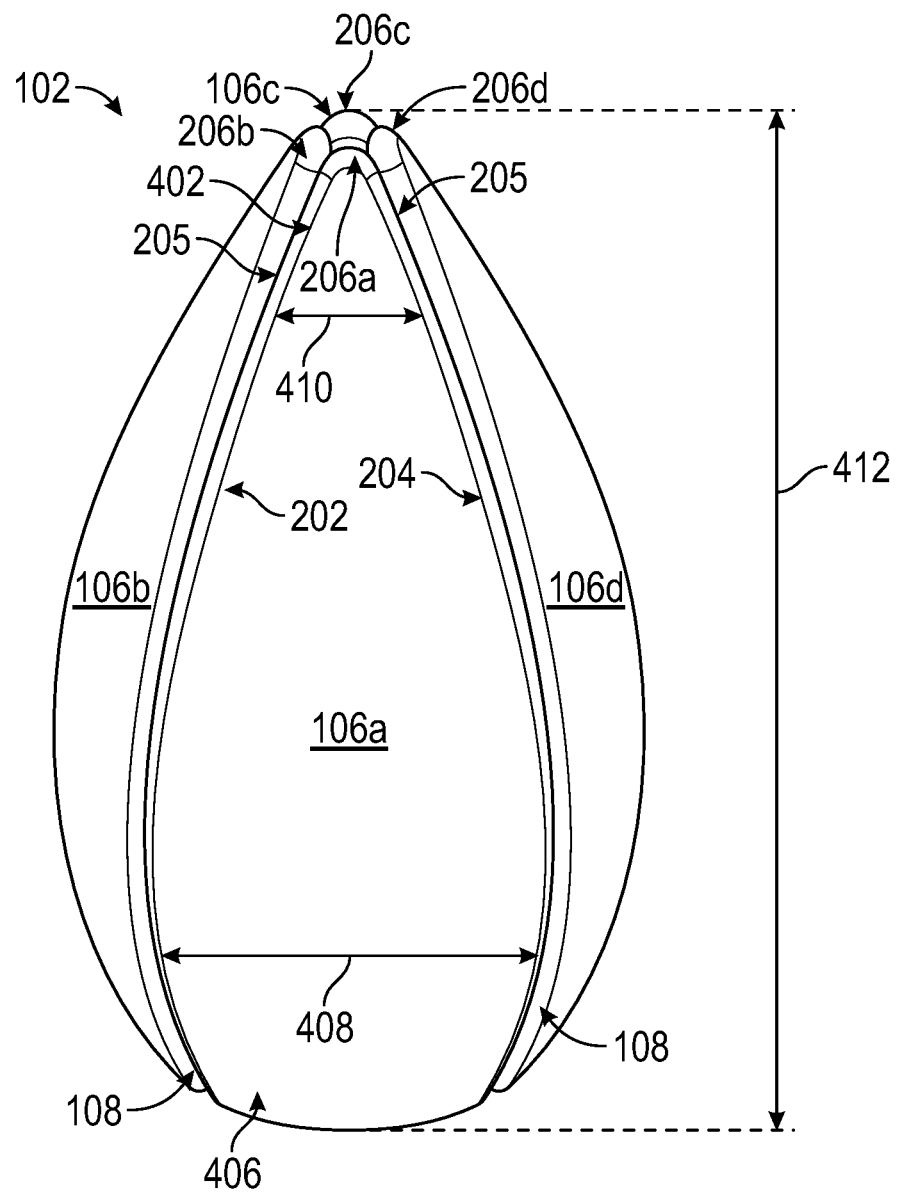
FIG. 4 depicts a pictorial illustration of the menstrual cup shown in FIG. 2 with the body of the menstrual cup shown in a closed position.

The menstrual cup 102 is configured to be in a fully open position and in a fully closed position. FIGS. 2-3 and FIGS. 5-7 depict the menstrual cup 102 in a fully open (expanded) position and FIG. 4 depicts the exemplary menstrual cup 102 in a fully closed (retracted) position. As shown in FIG. 4, the interior cavity 109 is not visible from the exterior or accessible to receive any fluids 114 as the interior cavity 109 would normally be in the fully open position. It may be useful for the menstrual cup 102 to be in the closed (retracted) position during insertion and removal of the menstrual cup 102 from the vaginal cavity or opening 112 of a woman's body so that the user experiences less pain or discomfort and to make it easier for the user to insert and remove the menstrual cup 102. Advantageously, the menstrual fluids 114 contained within the interior cavity 109 of the menstrual cup 102 will not leak out of the top or sides or bottom of the menstrual cup 102 when the menstrual cup 102 is in the closed position, which is a significant advantage over existing types of menstrual cups 102. It is very unhygienic, uncomfortable, and burdensome for the user when the user has to extract a full menstrual cup 102 if the menstrual fluid 114 contained within the menstrual cup 102 begins to leak and spill and has to be cleaned up by the user.

In a non-limiting embodiment, the body 104 of the menstrual cup is rather flexible, but still strong and durable. In a non-limiting embodiment, the menstrual cup 102 (including the body 104 and/or the hook 110) may be made of or include silicone in any of the parts of the menstrual cup 102. Other types of materials may also be used. For example, in a non-limiting embodiment, thermoplastic polyurethane (TPU) may also be used, which describes any class of polyurethane plastics. The materials utilized for the menstrual cup 102 are washable and designed to be reused and may have a good amount of elasticity. Silicone may be desirable because silicone can be washed and reused and is bendable and elastic while still being firm and strong.

In a non-limiting embodiment, the body 104 of the menstrual cup 102 may include one or more outer members 106 with one or more connecting walls 108 connecting each outer member 106 to form the body 104 of the menstrual cup 102. Further, the menstrual cup 102 may include a hook 110 on an underside or bottom surface of the body 104 of the menstrual cup 102. The hook 110 is designed to cause the body 104 and in particular the outer members 106 and connecting walls 108 to either expand or contract. This may be because if a user pushes upwardly on the hook 110, an upward force is transferred or applied to an underside of the body 104 of the menstrual cup 102, thereby causing the sides or outer members 106 of the body 104 of the menstrual cup 102 to open to an open, expanded position revealing the interior cavity 109 of the menstrual cup 102 and body 104. Conversely, if a user pulls downwardly on the hook 110, a downward force is transferred or applied to an underside of the body 104 of the menstrual cup 102, thereby causing the sides or outer members 106 of the body 104 of the menstrual cup 102 to close around the interior cavity 109 whereby the interior cavity 109 is not accessible and visible. In a non-limiting embodiment, the user may also need to push on one or more sides of the body 104 of the menstrual cup 102 with the user's fingers, such as pushing on one of the connecting walls 108 or the outer members 106 in order for the body 104 of the menstrual cup 102 to close inwardly. It is expected that the outer members 106 or sides of the body 104 of the menstrual cup 102 have some thickness and weight in order to stay in an open position or closed position. Further, it a non-limiting embodiment, the thickness of the outer members 106 may increase from the lower portion (e.g., lower section 406 to the upper section 402 as shown in FIG. 4 of the body 104 of the menstrual cup 102).

It is noted that in alternative embodiments, the user may apply a downward force or pulling action on the hook 110, which may cause the body 104 of the menstrual cup 102 to expand outwardly into a fully opened position. Conversely, in this alternative embodiment, when the user applies an upward force or pushing action the hook 110 the body 104 of the menstrual cup 102 may be triggered to contract inwardly and retract to a closed position.

As noted above, FIGS. 2-3 and FIGS. 5-7 show an exemplary menstrual cup 102 in an expanded and open position, while FIG. 4 shows the exemplary menstrual cup 102 in a closed contracted position. As shown in FIG. 2, the menstrual cup 102 has one or more outer members 106a, 106b, 106c, and 106d connected by connecting walls 108. In a non-limiting embodiment, there may be four outer members 106 including outer member 106a, 106b, 106c, and 106d as shown in FIG. 2.

Further, in a non-limiting embodiment, a connecting wall 108 is adjacent to each outer member 106. The left side 202 and right side 204 of each outer member 106 may contact a side edge of an adjacent connecting wall 108.

The top surfaces 206a, 206b, 206c, and 206d, as shown in FIG. 2, of each outer member 106a, 106b, 106c, and 106d may be curved in one or more non-limiting embodiments, although in other embodiments, the top surfaces 206a-206d may be straight and not curved or may have another shape or form.

The connecting walls 108 are configured to contract or bend inwardly. Each connecting wall 108 may include a seam (or joint) 205 that runs longitudinally down a front and back surface of the connecting walls 108. Each connecting wall 108 may include a generally centrally located seam 205 as well as one or more longitudinally oriented lines or ribs 210 that are generally parallel to the centrally located seam 205 on each connecting wall 108. The top of the seam 205 may join with a bottom of a triangular shaped piece 208 for each connecting wall 108 that facilitates the bending inwardly of the connecting wall 108 and the contracting or pulling inwardly of the outer members 106a, 106b, 106c, and 106d.

The outer members 106a, 106b, 106c, and 106d are generally distributed such that each outer member 106a, 106b 106c, and 106d is separated by a connecting wall 108. The edges of the connecting walls 108 touch or contact any adjacent outer members 106. As shown in FIG. 3, a bottom surface 302 of each outer member 106a, 106b, 106c, and 106d contacts an underside or bottom surface 304 of the body 104 of the menstrual cup 102.

As shown in the FIGS. 2-7, in a non-limiting embodiment, the outer member 106 may have a petal like shape, with a generally straight bottom edge 217 and generally curved side edges 202 and 204. The connecting walls 108 may facilitate the retraction and expansion of the body 104 of the menstrual cup 102 in coordination with the upward or downward forces transferred from the corresponding movement on the hook 110. In a non-limiting embodiment, the connecting walls 108 have a first side piece 216 and second side piece 218 on each side of the seam 205. Further, the top of the seam 205 joins with a triangular piece 208, whereby the triangular piece 208 is configured to be extended and visible when the body 104 of the menstrual cup 102 is in the expanded, open position. When the body 104 of the menstrual cup 102 is in the retracted, closed position, the triangular piece 208, first side piece 216, and second side piece 218 are not visible (e.g., as shown in FIG. 4). The connecting walls 108 are configured to enable the flexible bending inwards upon closing and then flexible bending outwards or expanding outwards upon opening of the body 104 of the menstrual cup 102 as caused by the pushing or pulling of the hook 110 that is attached to the underside 304 of the body 104 of the menstrual cup 102.

In one or more non-limiting embodiments, the body 104 of the menstrual cup 102 may be made separately from the hook body 214 and hook 110. In other non-limiting embodiments, the hook body 214 of the hook 110 (or the hook 110 of the menstrual cup 102) may be integrally formed with the body 104 of the menstrual cup 102.

As shown in FIG. 2 and FIG. 3, the hook 110 may include hook interior opening or cavity 212. The hook interior opening or cavity 212 may be particularly useful for one or more fingers or hands to grasp onto during insertion or removal or other manipulation of the menstrual cup 102. The hook 110 may include a hook body 214 that encircles or surrounds the hook opening 212. The user may insert their fingers into the hook opening 212 to grab onto the hook 110 and the menstrual cup 102 in general.

As shown in FIG. 3, the hook 110 may be generally attached to a central 306 location on the underside 304 of the body 104 of the menstrual cup 102 and beneath the outer members 106 and connecting walls 108. The underside 304 of the body 104 is closed and does not include any openings or holes so as to prevent any leakage of any contained menstrual fluids 114.

As shown in FIG. 4, the body 104 of the menstrual cup 102 is configured to contract so that the outer members 106a, 106b, 106c, and 106d contract and close to a fully closed position where the interior cavity 109 of the menstrual cup 102 is no longer accessible or visible. If there is any menstrual fluid 114 collected inside the body 104 of the menstrual cup 102 or in the interior cavity 109 of the menstrual cup 102, when the outer members 106a-106d are contracted and in a closed position, the menstrual fluids 114 would be enclosed and contained inside of the interior walls of the outer members 106 and the connecting walls 108 and could not leak or spill out through the top or sides or bottom.

As shown in FIG. 4, when closed, the top surfaces 206a, 206b, 206c, and 206d of each outer member 106a, 106b, 106c, and 106d may be brought in proximity with each other and may actually partially contact each other. The outer members 106a, 106b, 10c, and 106d may be designed to have a narrower upper section 402 and a wider lower section 406 or base. Accordingly, a width 408 of the lower section may be wider than a width 410 of the upper section 402. Further, in a non-limiting embodiment, the length 412 of each outer member 106 may be the same for each outer member 106.

As shown in FIG. 4, when in the closed position, the connecting walls 108 are fully contracted and bent inwards and the outer members 106a, 106b, 106c, and 106d are bent inwards also and are contacting each other or leaning on each other. The seams 205 of each connecting wall 108 may be visible from an exterior of the menstrual cup 102 in the contracted position in one or more non-limiting embodiments, but the majority of the surface of the connecting walls 108 may be bent inwardly towards an interior cavity 109 of the menstrual cup 102 so as to cause the body 104 and outer members 106 of the menstrual cup 102 to retract inwardly.

Figure 5:
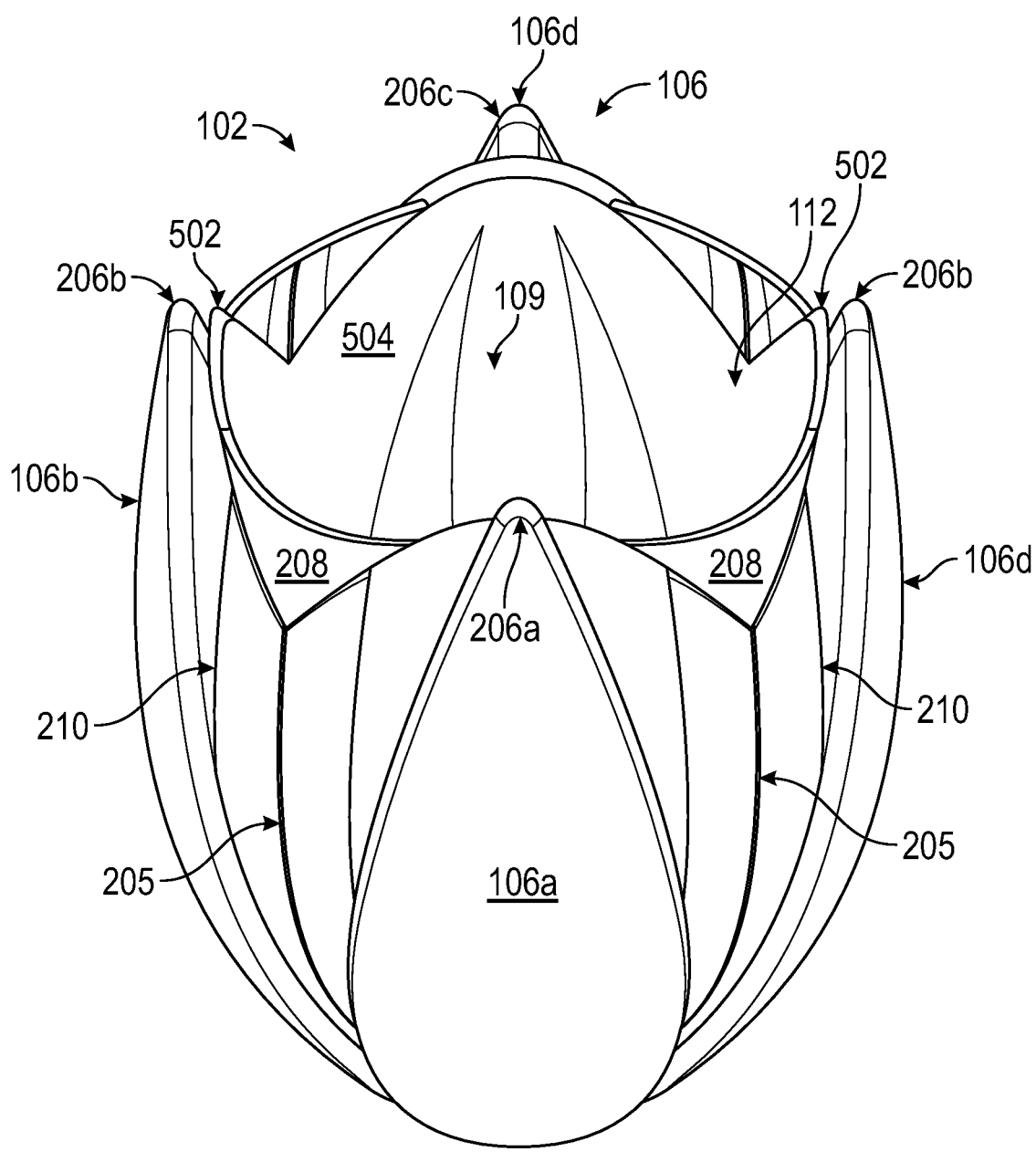
FIG. 5 depicts a pictorial illustration showing a top perspective view of the menstrual cup shown in FIG. 2 with a view of the interior cavity of the menstrual cup.

FIG. 5 may show a top perspective view of a body 104 of the menstrual cup 102 with a view of the interior cavity 109 of the menstrual cup 102. As shown in FIG. 5, there may be one or more interior protruding sections 502 that are behind each upper section of each outer member 106. The top surfaces 206a, 206b, 206c, and 206d may extend above or be taller than the height of the top of each protruding section 502. There may be a protruding section 502 for each outer member 106 and the protruding sections 502 may facilitate the bending inwardly and collapsing of the body 104 of the menstrual cup 102 in one or more non-limiting embodiments. It is noted in a non-limiting embodiment, the interior walls 504 of the menstrual cup 102 may be further lined or include additional protective covering or additional layer(s) of silicone so as to cover any interior cracks or openings shown in FIGS. 5-7.

Figure 6:
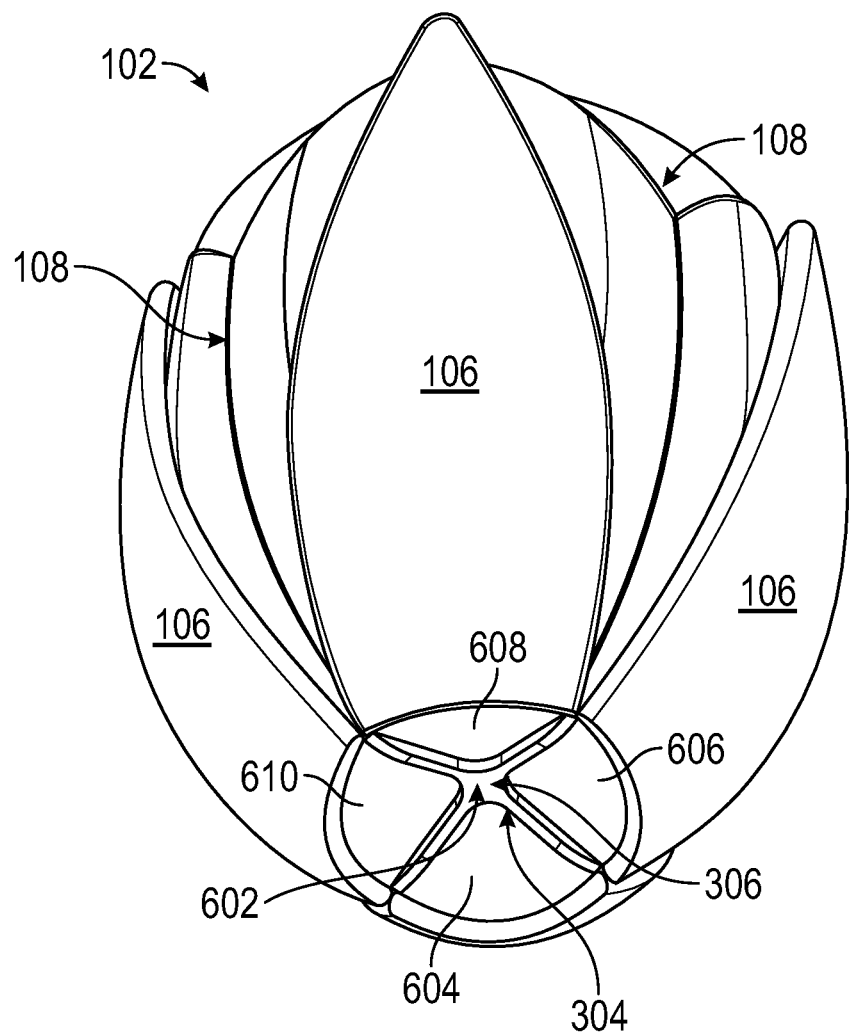
FIG. 6 depicts a pictorial illustration of a bottom of the menstrual cup shown in FIG. 2 without an attached hook.

FIG. 6 may show a bottom perspective view of a menstrual cup 102. The hook 110 is not pictured in FIG. 6 in order to provide a better view of the underside 304 of the body 104 of the menstrual cup 102. As shown in FIG. 6, the outer members 106 and the connecting walls 108 make up the semi-cylindrical body 104 shape of the menstrual cup 102. On the underside 304, there may be a rib piece 602 that extends across the underside 304 of the menstrual cup 104. The exemplary rib piece 602 shown in FIG. 6 may help increase the strength of the lower section of the body 104 of the menstrual cup 102 and further enable the collapsibility and retractability of the outer members 106 and the connecting walls 108. As shown in FIG. 6, the rib piece 602 may cause one or more identifiable sections 604, 606, 608, and 610 to form on the underside 304 of the body 104 of the menstrual cup. The rib piece 602 may protrude downwardly to a slight degree. As shown in FIG. 3, the top of the hook 110 may connect to a central 306 part of the underside 304 of the body 104 of the menstrual cup 102.

Figure 7:
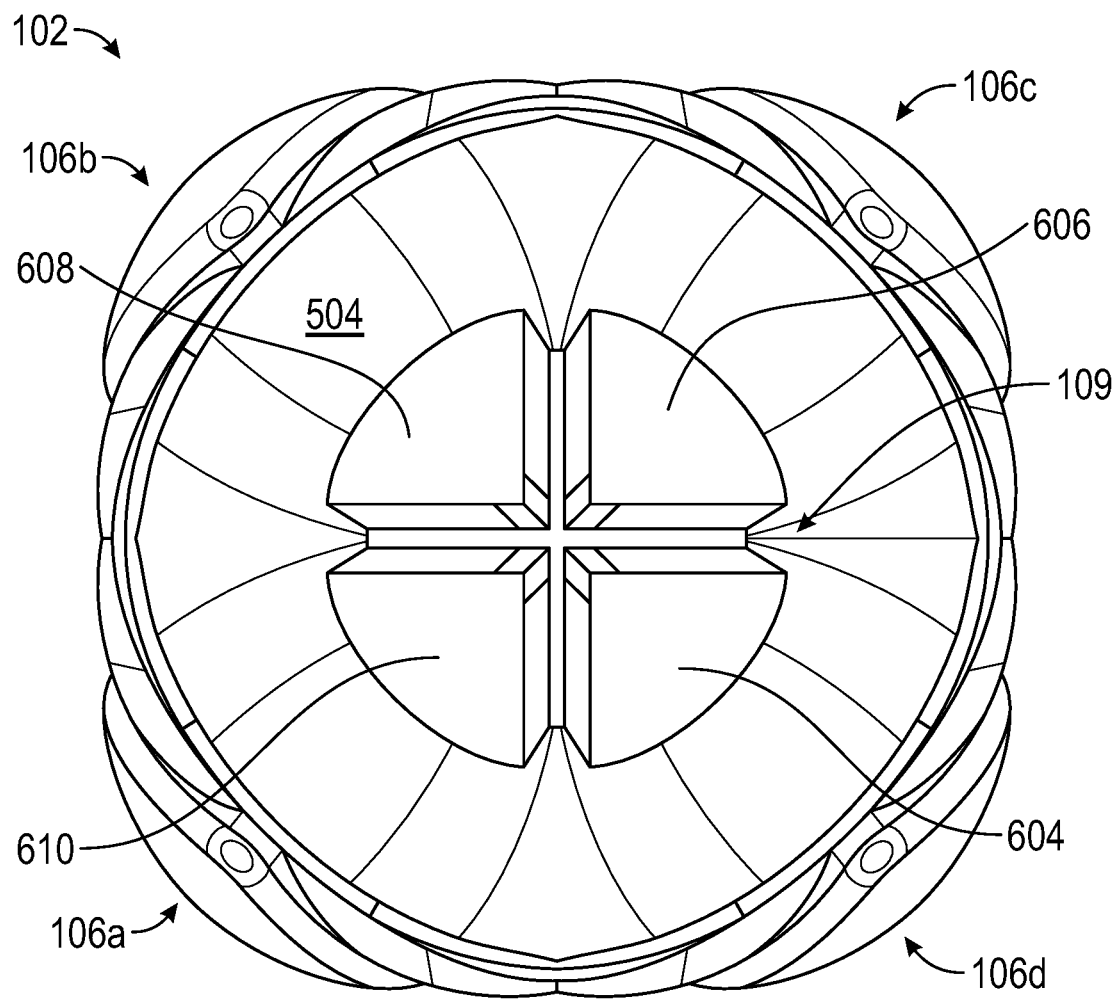
FIG. 7 depicts an interior view of the menstrual cup shown in FIG. 2.

FIG. 7 shows an exemplary interior view of the menstrual cup 102. As shown in a non-limiting embodiment, the menstrual cup 102 may include one or more projecting pieces corresponding to the identifiable sections 604, 606, 608, and 610 shown on the underside 304 of the body 104 of the menstrual cup 102. On the interior of the menstrual cup 102, the identifiable sections 604, 606, 608, and 610 may be separated from each other but still joined on the underside by the rib piece 602. The identifiable sections 604, 606, 608, and 610 may project inwardly when in an expanded, open position, and may project downwardly and outwardly when in a closed, retracted position. In a non-limiting embodiment, when the user grasps the hook 110 and pushes upwardly, the sections 604, 606, 608, and 610 may project inwardly also helping the outer members 106 and connecting walls 108 to expand outwardly to expose the interior cavity 109. In a non-limiting embodiment, when the user grasps the hook 110 and pulls downwardly, the sections 604, 606, 608, and 610 may project outwardly and help the outer members 106 and connecting walls 108 to retract inwardly and close around the interior cavity 109.

It is noted that as women may have different heaviness and rates of flow depending on the day of the menstrual cycle, the menstrual cup 102 may be made having different sizes to accommodate greater or lesser amounts of menstrual fluids 114 that may need to be contained within the interior cavity 109 of the menstrual cup 102. The menstrual cup 102 may be configured to fit within the vaginal opening 112 of a person (female) body.

Figure 8:
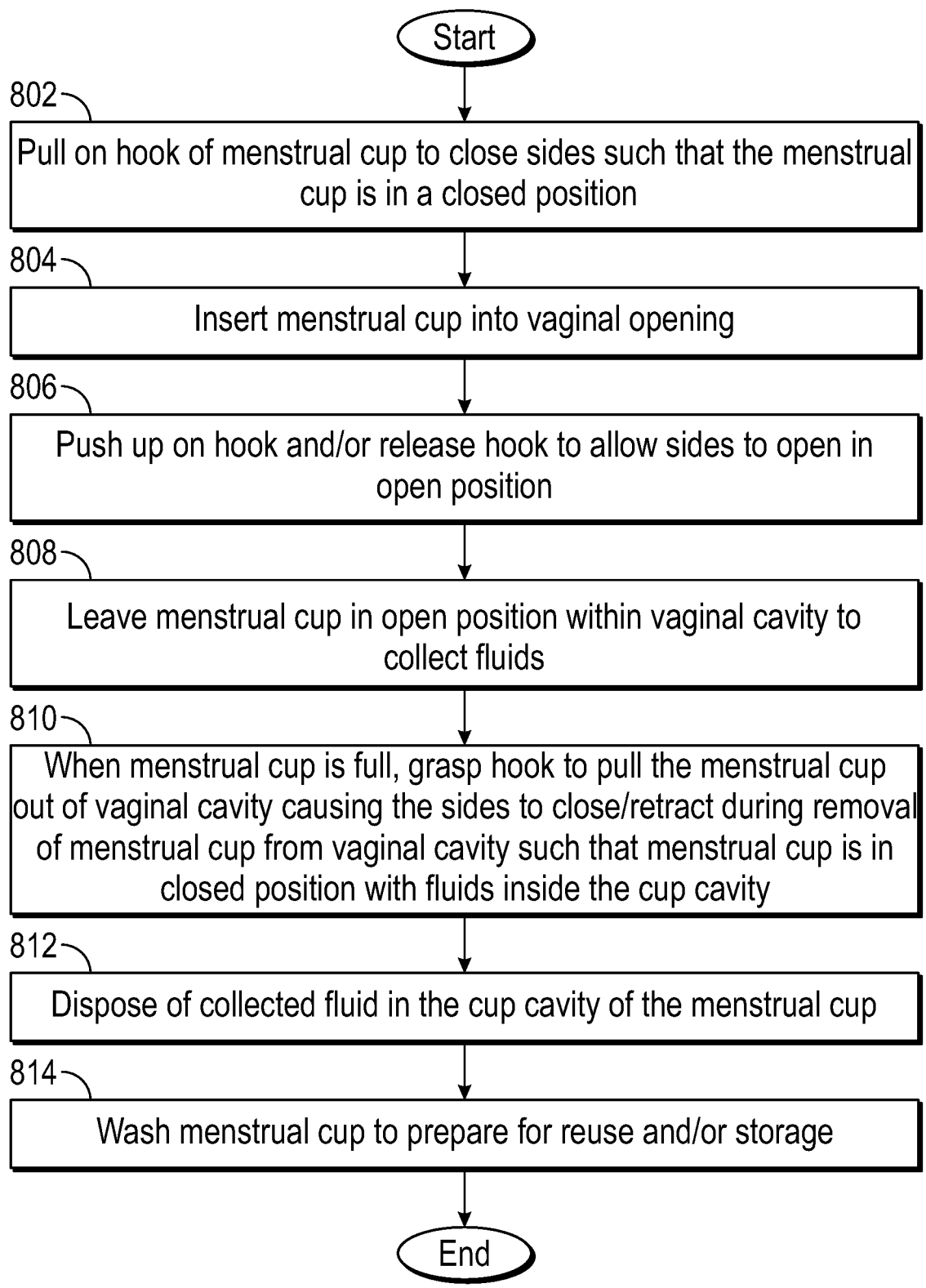
FIG. 8 depicts a flowchart of an exemplary method for using an expandable and retractable menstrual cup.

FIG. 8 provides an exemplary flowchart for using a menstrual cup 102 according to one or more non-limiting embodiments. In a non-limiting embodiment, at step 802, the user may pull on a hook 110 of a menstrual cup 102 to close the sides or outer members 106 and connecting walls 108 of the menstrual cup 102, such that the menstrual cup 102 is in a closed position. In a non-limiting embodiment, at step 804, the user may insert the menstrual cup 102 as a whole (including the hook 110) inside of the vaginal opening or cavity 112. It is recommended that prior to insertion into the vaginal cavity 112, that the body 104 of the menstrual cup 102 be in the retracted, closed position. Accordingly, while the menstrual cup 102 is outside of the user's body and outside of the vaginal cavity 112 of the user's body, the user would pull on the hook 110 of the menstrual cup 102 to cause the body 104 of the menstrual cup 102 to close and contract.

At step 806, the user may push up on the underside 304 of the body 104 and release the hook 110 of the menstrual cup 102 to cause the outer members 106 and connecting walls 106 and/or body 104 of the menstrual cup 102 to expand to the open position. When the menstrual cup 102 is in the open position within the vaginal cavity 112 of the user's body, the menstrual cup 102 is made ready to receive and contain any menstrual fluids 114 that flow into the interior cavity 109 of the menstrual cup 102. Accordingly, as shown at step 808, the user may leave the menstrual cup 102 in its open position within the vaginal cavity 112 to collect any menstrual fluids 114.

At step 810, the user may want to remove the menstrual cup 102. Typically, this may be because the menstrual cup 102 feels full to the user. To remove the menstrual cup 102, the user may grasp the hook 110 to pull the menstrual cup 102 out of the vaginal cavity 112 which should also cause the hook 110 to apply a downward force on the body 104 of the menstrual cup 102, thereby causing the body 104 (e.g., the outer members 106 and the connecting walls 108) to contract into a closed position and to close around the interior cavity 109 of the menstrual cup 102. Accordingly, during removal of the menstrual cup 102, the menstrual cup 102 is in the closed position and any contained menstrual fluids 114 are enclosed by the body 104 (e.g., the outer members 106 and the connecting walls 108) of the menstrual cup 102. In this manner, the menstrual fluids 114 do not leak out of the body 104 of the menstrual cup 102. At step 812, the user may dispose of any collected fluids 114, which can be done be disposing of them in a toilet bowl and flushing them away or in a trash can for example. At step 814, the user can wash and sanitize the menstrual cup 102 to prepare for reuse of the menstrual cup 102 in the vaginal cavity 112 of the user or may store the menstrual cup 102 for future use.

The menstrual cup 102, as described herein, offers many advantages including the comfort and reassurance to the user who will be able to immediately know when the menstrual cup 102 is fully expanded within the vaginal cavity and when the menstrual cup 102 is closed, which is an issue many users of commonly available menstrual cups 102 complain about in that the users are never sure if the menstrual cup 102 is properly inserted or not.

Further, the user will not want any menstrual fluid to spill or leak when the menstrual cup 102 is being pulled out of the vaginal cavity. The ability for the menstrual cup 102, as described in one or more non-limiting embodiments, to contract when the user pulls the hook 110 of the menstrual cup 102, causing the sides or outer members 106 of the body 104 of the menstrual cup 102 to contract provides peace of mind to the user when using the menstrual cup 102 that any messiness and unhygienic spilling of the menstrual fluids on the user or the floor can be avoided. The use of menstrual cup 102 helps the environment and prevents the use of single use plastic tampons, pads, or other such feminine hygiene products which cannot be recycled or reused and contribute to the environmental challenges and crisis that is currently a high priority. Further, menstrual cup 102 may be advantageous over other feminine hygiene products because menstrual cup 102 may cause less discomfort than a tampon or a pad. Further, the user has a greater peace of mind that the menstrual cup 102 will stay in place and capture any menstrual fluids without leaking. Many other advantages and benefits may be offered by the menstrual cup 102 as described above and shown in the attached Figures.

In the Summary above and in this Detailed Description, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, and steps, among others, are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm and upper limit is 100 mm.

Certain terminology and derivations thereof may be used in the following description for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "coupled to" as used herein may refer to a direct or indirect connection. The term "set" as used herein may refer to one or more items. Accordingly, "set" may refer to a singular item or to a plurality of items.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention.

The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description is to be regarded as illustrative instead of restrictive of the present invention.

What is claimed is:

1. A method of using a menstrual cup, the method comprising:
   providing the menstrual cup, the menstrual cup comprising:
      a flexible body having an interior cavity, wherein the flexible body is configured to open to an open position and to close and retract to a closed position; and
      a hook attached to a bottom surface located on an underside of the flexible body,
      wherein a downward force exerted by the hook on the flexible body causes the flexible body to contract and close inward such that a set of sides or a set of outer members of the flexible body are brought towards each other covering the interior cavity, and
      wherein an upward force exerted by the hook on the flexible body causes the flexible body to gradually expand outward such that the set of sides or the set of outer members of the flexible body expand outwards to a fully open position and exposes the interior cavity of the menstrual cup;
   pulling the hook of the menstrual cup to close the set of sides or the set of outer members of the menstrual cup in order for the menstrual cup to be in the closed position;
   inserting the menstrual cup in the closed position into a vaginal cavity in the human body;
   upon positioning the menstrual cup at a desired spot within the vaginal cavity, pushing upwards on the hook causing the set of sides or the set of outer members of the menstrual cup to fully expand while positioned inside the vaginal cavity;
   upon removal of the menstrual cup, grasping the hook the hook to pull the menstrual cup out of the vaginal cavity causing the set of sides or the set of outer members to close or retract during removal of the menstrual cup and any collected menstrual fluids or other bodily fluids within the menstrual cup are contained by the set of sides or the outer members of the menstrual cup;
   disposing of the any collected menstrual fluids or other bodily fluids collected in the internal cavity of the menstrual cup; and
   reusing the menstrual cup if needed or storing the menstrual cup for future use.

2. The method of claim 1, further comprising, upon insertion through the vaginal cavity, causing the set of sides or set of outer members to close inwardly prior to insertion of the menstrual cup in the vaginal cavity or opening.

3. The method of claim 1, further comprising, upon removal of the menstrual cup from the vaginal cavity, causing the set of sides or set of outer members to close inwardly and then removing the menstrual cup from the vaginal cavity.

4. The method of claim 1, further comprising, washing or sanitizing the menstrual cup prior to reuse.

5. The method of claim 1, wherein the flexible body and the hook comprise silicone.

6. The method of claim 1, wherein the hook comprises a hook cavity and a hook body surrounding the hook cavity.

* * * * *